United States Patent [19]
Ohlsson

[11] 3,991,748
[45] Nov. 16, 1976

[54] CIRCUIT ARRANGEMENT FOR THE PROCESSING OF PHYSIOLOGICAL MEASURING SIGNALS

[75] Inventor: Thomas Ohlsson, Vallingby, Sweden

[73] Assignee: Siemens Aktiengesellschaft, Erlangen, Germany

[22] Filed: June 19, 1975

[21] Appl. No.: 588,464

[30] Foreign Application Priority Data
June 21, 1974 Germany............................ 2429955

[52] U.S. Cl............................................. 128/2.06 B
[51] Int. Cl.²......................................... A61B 5/04
[58] Field of Search................. 128/2.06 B, 2.06 G, 128/2.06 R, 2.1 R

[56] References Cited
UNITED STATES PATENTS

| | | | |
|---|---|---|---|
| 2,684,278 | 7/1954 | Marchand | 128/2.06 B |
| 3,709,212 | 1/1973 | Koeblitz | 128/2.06 B |
| 3,868,948 | 3/1975 | Graetz | 128/2.06 B |
| 3,882,846 | 5/1975 | Fletcher | 128/2.06 B |

OTHER PUBLICATIONS

Duffin, Jr. et al., "Proceedings of the 23rd Annual Conference on Engineering in Medicine & Biology," Wash., D.C. Nov. 16–19, 1970, p. 193.

*Primary Examiner*—William E. Kamm
*Attorney, Agent, or Firm*—Haseltine, Lake & Waters

[57] ABSTRACT

A circuit arrangement for the processing of physiological measuring signals, including a plurality of input amplifiers having branch signal electrodes connected thereto and to which there are subsequently connected differential amplifiers, each of the latter being connected to the outputs of at least two input amplifiers by means of a program selector and pursuant to a preselected program, and in which it becomes possible to effect a screening or testing of the various circuit elements and, thereby, also of the input amplifiers. A manually controllable calibrating impulse generator is connected to the inputs of all input amplifiers so as to increase the input voltages of the input amplifiers, each differential amplifier including an additional calibrating input to which there is transmissible a calibrating signal from the calibrating impulse generator and wherein, in each differential amplifier, the signal at the calibrating input is superimposed on the differential signal.

6 Claims, 3 Drawing Figures

3,991,748

CIRCUIT ARRANGEMENT FOR THE PROCESSING OF PHYSIOLOGICAL MEASURING SIGNALS

FIELD OF THE INVENTION

The present invention relates to a circuit arrangement for the processing of physiological measuring signals.

In an electrocardiograph, the requirement is present that calibrating impulses can be superimposed on the signals which control the EKG reproduction arrangement, and which appear in the output channels facilitating, on the one hand, determination of the magnitude of the EKG signals and, on the other hand, allowing for the screening of the circuit elements in individual channels, in effect meaning, providing an indication of the damaging of any one of these circuit elements.

SUMMARY OF THE INVENTION

Accordingly, it is an object of the present invention to provide a circuit arrangement for the processing of physiological measuring signals, including a plurality of input amplifiers having branch signal electrodes connected thereto and to which there are subsequently connected differential amplifiers, each of the latter being connected to the outputs of at least two input amplifiers by means of a program selector and pursuant to a preselected program, and in which it becomes possible to effect a screening or testing of the various circuit elements and, thereby, also of the input amplifiers.

The foregoing object is inventively solved in that a manually controllable calibrating impulse generator is connected to the inputs of all input amplifiers so as to increase the input voltages of the input amplifiers, each differential amplifier including an additional calibrating input to which there is transmissible a calibrating signal from the calibrating impulse generator and wherein, in each differential amplifier, the signal at the calibrating input is superimposed on the differential signal. In the inventive arrangement, upon activation of a calibrating switch, the input signal at all input amplifiers is magnified so that these, and all circuit elements subsequently connected thereto, may be tested. The calibrating signal is recorded by the reproducing arrangement and allows for a determination of the magnitude of the recorded measured value signals.

The invention further provides a circuit arrangement affording the advantage that the calibrating signal does not appear when the calibrating impulse generator does not increase the input voltage of the input amplifiers so as to be erroneous.

In accordance with a further aspect of the invention, the output signal of at least one of the input amplifiers is compared with the calibrating signal by a differential amplifier so that a correct output signal appears at the output of the differential amplifier only when these two signals are equal to each other. In most EKG programs for three or six reproduction or recording installations, this compared input signal is transmitted also to another differential amplifier wherein it is compared with still another input signal. This input signal thus must also appear like the calibrating signal when faultless constructional components are present.

BRIEF DESCRIPTION OF THE DRAWINGS

Reference may now be had to the following detailed description of two exemplary embodiments of the invention, taken in conjunction with the accompanying drawings; in which.

DETAILED DESCRIPTION

The hereinillustrated embodiments are employed for the obtention of the electrocardiogram of a patient.

Figure 1:
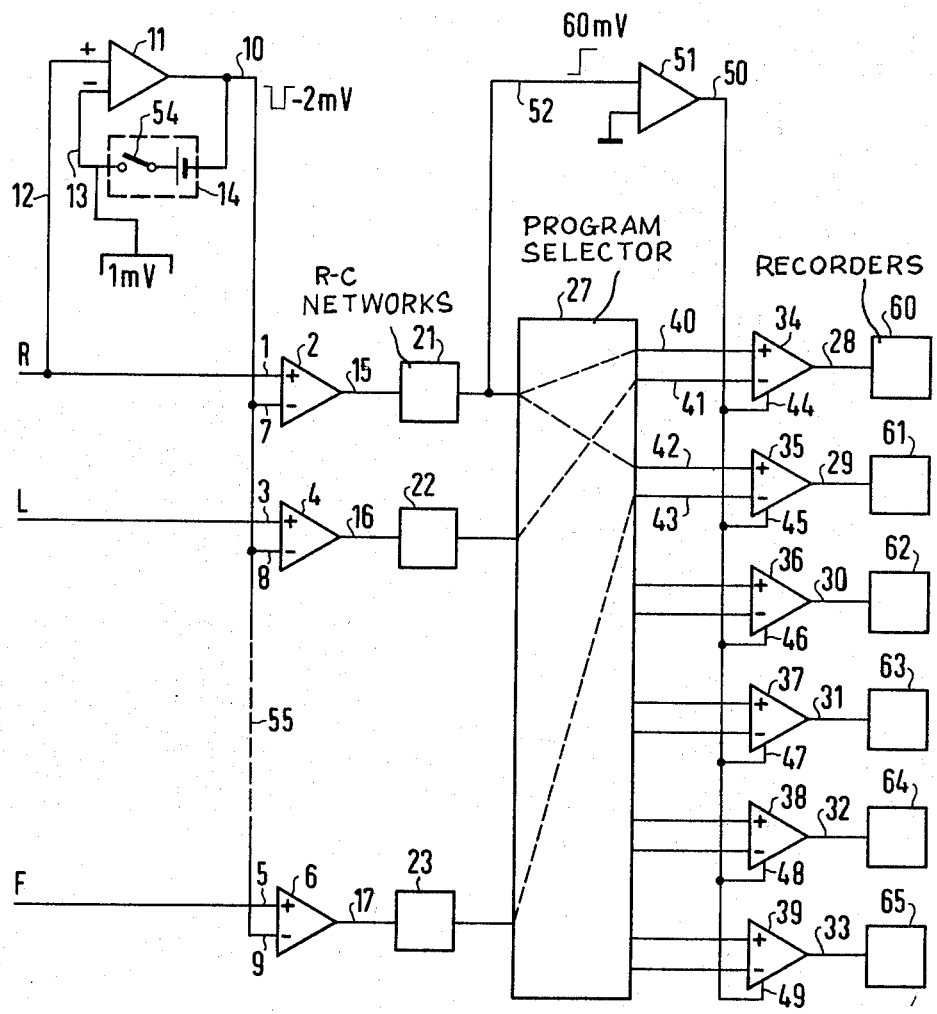
FIG. 1 shows a first embodiment of a circuit arrangement pursuant to the present invention.

Illustrated in FIG. 1 are three input channels or conduits R, L and F, which lead to, respectively, three electrodes positioned on the body of a patient, namely, on the left and right arm, and on one foot. Additionally leading to these three input channels, in a known manner, are the input channels or conduits for electrodes which are fastened to the chest wall of the patient, and which are omitted from the drawings for purposes of clarity. The input R leads to the input 1 of a differential amplifier 2, the input L to the input 3 of a differential amplifier 4, and the input F to the input 5 of a differential amplifier 6. The inputs 1, 3 and 5 hereby all possess the same polarity. The second inputs 7 through 9 of the differential amplifiers 2, 4 and 6 are interconnected to each other and are located at the output 10 of an impedance transformer 11 which has its input 12 connected with the input channel or conduit R. The input 13 of the impedance transformer leads to a calibrating circuit 14. The impedance transformer 11 possesses a high input resistance and a low output resistance, so that the electrode which is associated with the input circuit R is not burdened by the differential amplifiers 2, 4 and 6.

The reference potential of the input circuit is the output potential of the impedance transformer 11 in the conduit 10. This output potential has the same interference or static signals superimposed or impressed thereon which lie also at the inputs R, L and F. Since the input amplifiers 2, 4 and 6 are differential amplifiers, they do not amplify the interference or static signals but only the differential signals, so that the signals at the outputs 15 through 17 are freed of interference signals.

For effecting the separation of direct-current voltage potentials, RC-elements (Resistance Capacitance networks) 21 through 23 are connected to the outputs 15 through 17.

The outputs of the RC-elements 21 through 23 are connected to a program selector 27. With regard to the previously described input circuit, it is to be maintained that the reference potential of this input circuit is branched off from the collector electrode for the EKG and that this reference potential serves for the entire input circuit up to the program selector 27, whereby interference signals (static) may be suppressed to an appreciable extent.

The program selector 27 has six output channels or conduits 28 through 33 associated therewith, and which lead to six EKG reproducing arrangements 60 through 65, for example, to six recorders. A recorder which may be utilized herein is described, for example, in Canadian Pat. No. 513,848. Each of the output channels 28 through 33 extends from a differential amplifier 34 through 39. The differential amplifiers 34 through 39 each possess two inputs to which there is transmittable, by means of the program selector 27, the output signal of two input amplifiers. Selectable at the program selector 27, are the programmed output pairs of the input amplifiers for each subsequently connected differential amplifier 34 through 39. Indicated, for example, by the phantom lines in program selector 27, is that the differential amplifier 34 receives at its input 40 the output signal of the input amplifier 2 and receiver at its input 41 the output signal of the input amplifier 4. In this example, the differential amplifier 35 receives at its input 42 the output signal of the input amplifier 2, and at its input 43 receives the output signal of the input amplifier 6.

In the illustrated embodiment, the differential amplifier 34 forms the difference between the output signals of the input amplifiers 2 and 4, and thereby delivers a signal at its output 28 which corresponds to this difference. The differential amplifier 35 forms the difference between the output signals of the input amplifiers 2 and 6. By means of the further differential amplifiers 36 through 39, in accordance with the program selected at the program selector 27, there is similarly effected the formation of the differential between respectively two output signals of the input amplifiers.

In an electrocardiograph there is provided the requirement that the latter can be calibrated, in effect meaning, that the signals at the outputs 28 through 33 may have calibrating impulses impressed or superimposed thereon which characterize on the other hand, a predetermined voltage amplitude and, on the other hand, facilitate that testing may be carried out as to whether all amplifying channels operate satisfactorily, in effect, whether a constructional component is defective or not.

For this purpose, the differential amplifiers 34 through 39 each possess calibrating inputs 44 through 49 which commonly lie at the output 50 of an amplifier 51. The amplifier 51 has transmitted to the input 52 thereof the output signal of the input amplifier 2. The output signal of amplifier 2 has no D.C. component.

When there is actuated a calibrating switch key or push-button 54 in the calibrating circuit 14, there then varies the reference potential at the output 10 of the impedance transformer 11. Inasmuch as, by means of differential amplifiers 34 through 39, there is formed the difference between respectively two output signals of the input amplifier are formed, through variation of the reference potential in the conduit 10, no variation of the output signals at the outputs 28 through 33 is effected when the input amplifiers are in good working order. However, when an input amplifier is damaged, an error signal will appear in at least one of the output channels. It is naturally a prerequisite that the defective input amplifier be employed in the program which has been selected at the program selector 27. However, the output signals of all input amplifiers vary, and thereby also that of the amplifiers 2 and consequently the signal at the input 52 of the amplifier 51.

At the output 50 there thus appears a calibrating impulse which is superimposed on the signals provided by the differential amplifiers 34 through 39 through the differential formation, and thereby also similarly appears at the outputs 28 through 33 as a calibrating impulse. The calibrating impulses at the outputs 28 through 33, when the electrocardiograph is in order, must be equally large at all outputs and must possess the same polarity. If this is not the case, then closing off may be effected with respect to the presently damaged channel. Furthermore, the calibrating impulses facilitate a comparison of the EKG signals with a reference voltage.

The phantom or chain-dotted line 55 signifies that further input amplifiers lie between the input amplifiers 2, 4 and 6 which are associated with the further electrodes, namely, the chest wall electrodes. These further amplifiers, in a preprogramming manner, are connected through the program selector 27 to the differential amplifiers 36 through 39.

The impedance transformer 11 possesses a voltage amplification of one, whereas the voltage amplification of the input amplifiers 2, 4 and 6, for example, may be thirty. Present at the input 52 of the amplifier 51, upon actuation of the calibrating push-button 54, for example, is an impulse of 60mV when a calibrating impulse consists of 2mV. The amplification of the amplifier 51 is so selected that this calibrating impulse generates a calibrating signal at the outputs 28 through 33 which correspond to an EKG signal of 1mV. Due to this 2mV-echo impulse larger error signals are obtained at the outputs 28 through 33 than would be in the utilization of 1mV-echo impulses, when one or more input amplifiers are damaged.

The circuit arrangement according to FIG. 1, upon actuation of the calibrating push-button 54, allows for testing of all circuit components. The calibrating voltage is hereby introduced at the minus input of the differential amplifiers 2, 4 and 6. If no interference impulses are encountered in the EKG, then with a great degree of certainty it may be assumed that the plus or positive inputs of the differential amplifiers 2, 4 and 6 are also in order.

Figure 2:
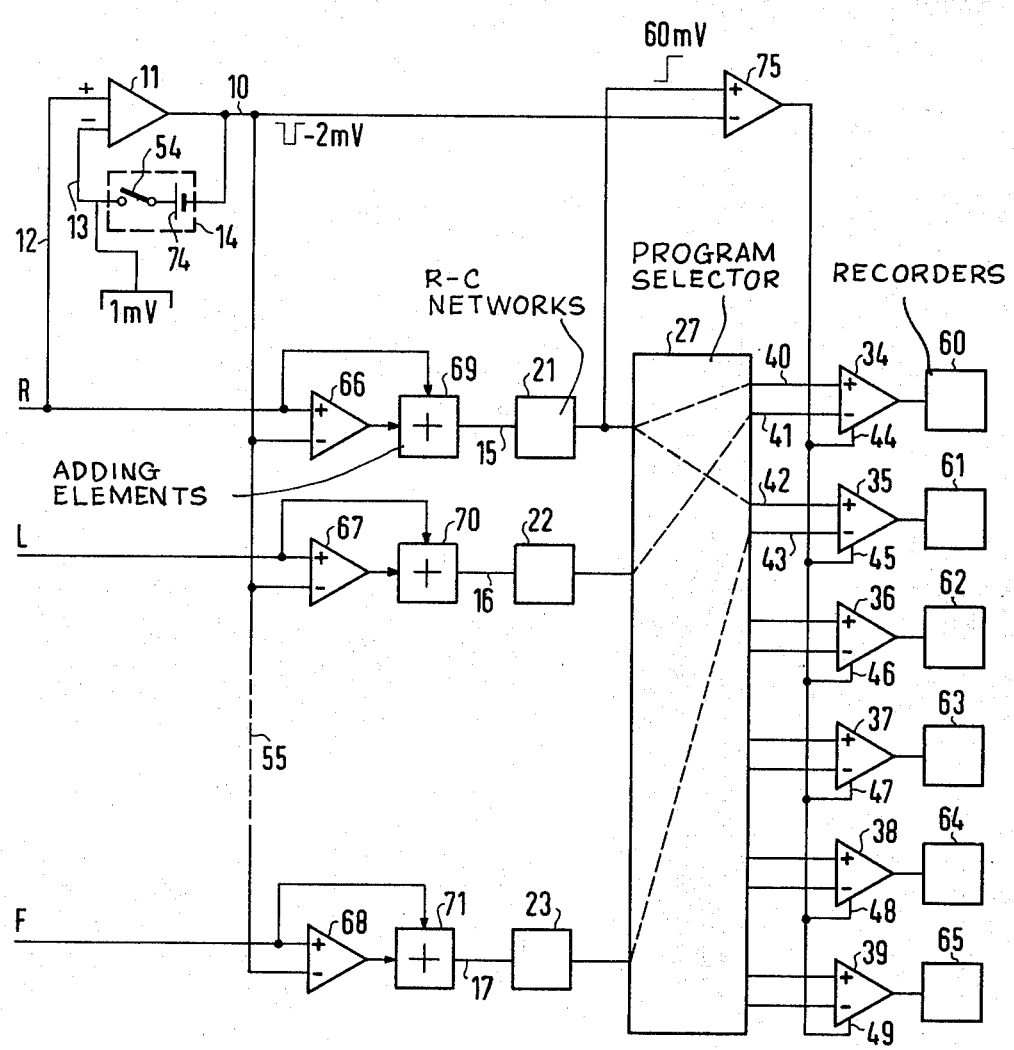
FIG. 2 shows a second embodiment of a circuit arrangement according to the invention.

In the exemplary embodiment according to FIG. 2, components which are identical with the components of the example according to FIG. 1 are designated by the same reference numerals. Utilized hereby as the input amplifiers are differential amplifiers 66 through 68 which are interconnected with adding elements 69 through 71 in the illustrated manner. The input amplifiers, in connection with the adding elements, effect that the differential voltages between the branch electrodes, as amplified by the amplification factor of the amplifiers 66 through 68 (for example, 30 times), are detected through differential amplifiers 34 through 39, but that in-phase signals (static hum) are not amplified so as to thereby again appear in the output conduits 15 through 17. They are thus eliminated in the differential formation in the differential amplifiers 34 through 39. Tolerances of the construction components of the input circuit thereby do not enter into the in-phase signal suppression.

The calibrating circuit, also in this instance, contains an impedance transformer which is connected to the branch electrode R, and which has a calibrating push-button 54 associated which may connect a direct-voltage source 74 to the impedance transformer 11, and thereby raise the common reference potential of the minus or negative inputs of the amplifiers 66 through 68. The 2mV output impulse of the impedance transformer 11, which appears upon actuation of the calibrating push-button 54, is also transmitted to a differential amplifier 75 at the minus input thereof. At its plus input, the differential amplifier 75 receives the output signal of the input amplifier 66 which, at 30 times amplification, consists of 60mV. The differential voltage of 62 mV, as in the embodiment according to FIG. 2, influences the differential amplifiers 34 through 39.

Figure 3:
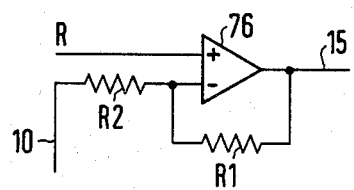
FIG. 3 shows a circuit detail of the embodiment of FIG. 2.

The constructional components 66, 69; 67, 70 and 68, 71 may also be built in conformance with FIG. 3. Thus, for example, the R-branch electrode may be connected to an operational amplifier 76 which two resistance R1 and R2 associated therewith in the illustrated manner. In the same manner may also be constructed the other input amplifiers. Each input amplifier is, in this instance, also an operational amplifier, and the electrodes are connected to the plus inputs of all operational amplifiers. Between the minus inputs and the outputs of the operational amplifiers there are located equally large resistances R1. The second inputs are further connected through equally large resistances R2 with a common potential junction which is connected to the conduit 10, and thereby to the output of the impedance transformer 11.

The invention is described in connection with an electrocardiograph. However, for example, it is also equally applicable for use in an EEG apparatus.

While there has been shown what is considered to be the preferred embodiment of the invention, it will be obvious that modifications may be made which come within the scope of the disclosure of the specification.

What is claimed is:

1. In a circuit arrangement for the processing of physiological measuring signals, a plurality of input amplifiers; branch signal electrodes being connected to said input amplifiers; and a program selector for connecting differential amplifiers to the outputs of at least two of said input amplifiers pursuant to a selected program, the improvement comprising: calibrating impulse generator means being connected to the inputs of all of said input amplifiers for raising the input voltages of said input amplifiers; means connecting said differential amplifiers to said calibrating impulse generator means, each said differential amplifier having a further calibrating input for receiving a calibrating signal from said calibrating impulse generator means, said signal at the calibrating input being superimposed on the differential signal in each said differential amplifier; and means for connecting the outputs of said differential amplifiers to recording means.

2. A circuit arrangement as claimed in claim 1, said calibrating signal being branched off from the signal transmitted to said input amplifiers through said calibrating impulse generator means.

3. A circuit arrangement as claimed in claim 2, said calibrating signal being branched off at an input amplifier operatively connected to at least one said differential amplifier.

4. A circuit arrangement as claimed in claim 3, said input amplifiers comprising differential amplifiers having equally-poled first inputs connected to said branch electrodes; a reference electrode, said differential amplifiers having second inputs collectively connected with said reference electrode said calibrating impulse generator means being located intermediate the common junction of said second inputs and said reference electrode.

5. A circuit arrangement as claimed in claim 3, each said input amplifier comprising an operational amplifier, said electrodes being connected to positive inputs of said operational amplifiers; resistances being connected between negative inputs and outputs of said operational amplifier; second resistances being positioned between a common potential juncture of said negative inputs and said inputs; a common reference electrode being connected to said common potential juncture; an impedance transformer being interposed between said reference electrode and said potential juncture; said calibrating impulse generator means including means for raising the output voltage of said impedance transformer; and a differential amplifier for forming the calibrating signal transmitted to said calibrating inputs, said differential amplifier being connected to said common potential juncture and to the output of that input circuit having said reference electrode located therein.

6. A circuit arrangement as claimed in claim 1 wherein said calibrating signal is branched off from the signal transmitted to said input amplifiers through said calibrating impulse generator means; said calibrating signal being branched off at an input amplifier operatively connected to at least one said differential amplifier; said input amplifiers comprising differential amplifiers having equally-poled first inputs connected to said branch electrodes, a reference electrode, said differential amplifiers having second inputs collectively connected with said reference electrode, said calibrating impulse generator means being located intermediate the common junction of said second inputs and said reference electrode; each said input amplifier comprising an operational amplifier, said electrodes being connected to positive inputs of said operational amplifiers; resistances being connected between negative inputs and outputs of said operational amplifier; second resistances being positioned between a common potential juncture of said negative inputs and said inputs; a common reference electrode being connected to said common potential juncture; an impedance transformer being interposed between said reference electrode and said potential juncture; said calibrating impulse generator means including means for raising the output voltage of said impedance transformer; and a differential amplifier for forming the calibrating signal transmitted to said calibrating inputs, said differential amplifier being connected to said common potential juncture and to the output of that input circuit having said reference electrode located therein.

* * * * *